(12) United States Patent
Stensen et al.

(10) Patent No.: US 9,212,202 B2
(45) Date of Patent: Dec. 15, 2015

(54) METHODS OF PEPTIDE MODIFICATION

(75) Inventors: Wenche Stensen, Kvaloysletta (NO); Oystein Rekdal, Hvalstad (NO); John Sigurd Svendsen, Kvaloysletta (NO)

(73) Assignee: Lytix Biopharma AS, Tromsø (NO)

( * ) Notice: Subject to any disclaimer, the term of this patent is extended or adjusted under 35 U.S.C. 154(b) by 1223 days.

(21) Appl. No.: 12/808,917

(22) PCT Filed: Dec. 22, 2008

(86) PCT No.: PCT/GB2008/004244
§ 371 (c)(1),
(2), (4) Date: Feb. 28, 2011

(87) PCT Pub. No.: WO2009/081151
PCT Pub. Date: Jul. 2, 2009

(65) Prior Publication Data
US 2011/0143384 A1    Jun. 16, 2011

(30) Foreign Application Priority Data
Dec. 20, 2007 (GB) .................................. 0724953.5

(51) Int. Cl.
*C12Q 1/37* (2006.01)
*C07K 1/06* (2006.01)
*C07K 7/00* (2006.01)
*C07K 1/107* (2006.01)

(52) U.S. Cl.
CPC ............... *C07K 1/062* (2013.01); *C07K 1/1077* (2013.01)

(58) Field of Classification Search
CPC ....... A61K 38/04; A61K 38/10; A61K 38/08; A61K 31/00; A61K 35/74; A61K 38/03; A61K 49/0056; C07K 7/08; C07K 7/06; C07K 14/4723; C07K 14/195; C07K 7/02; C07K 16/1267; C12N 2310/3515
See application file for complete search history.

(56) References Cited

PUBLICATIONS

Olson et al. Trypsin cleaves exclusively C-terminal to arginine and lysine residues. Mol Cell Proteomics. Jun. 2004;3(6):608-14.*
STN (RN 173287-93-9) 1996.*
JC Piard, M Desmazeaud Inhibiting factors produced by lactic acid bacteria. 2. Bacteriocins and other antibacterial substances. Lait 1992; 72:113-142.*
Basak et al. Aminoethyl benzenesulfonyl fluoride and its hexapeptide (Ac-VFRSLK) conjugate are both in vitro inhibitors of subtilisin kexin isozyme-1. FEBS Letters 573 (2004) 186-194.*
Brinckerhoff et al., "Terminal modifications inhibit proteolytic degradation of an immunogenic MART-1(27-35) peptide: implications for peptide vaccines," International Journal of Cancer (Oct. 29, 1999): vol. 83, No. 3; pp. 326-334.
Bengt Erik Haug, "Antibacterial peptides containing non-coded aromatic amino acids," University of Tromso, XP007909093 (Chapter 4.6 and Paper IV) (May 1, 2002).
Svenson et al., "Albumin binding of short cationic antimicrobial micropeptides and its influence on the in vitro bactericidal effect," Journal of Medicinal Chemistry (Jul. 12, 2007): vol. 50, No. 14; pp. 3334-3339.
Svenson et al.,"Antimicrobial peptides with stability toward tryptic degradation," Biochemistry (Mar. 25, 2008): vol. 47, No. 12; pp. 3777-3788.
International Search Report and Written Opinion issued for PCT/GB2008/004244.

* cited by examiner

*Primary Examiner* — Karlheinz R Skowronek
*Assistant Examiner* — Jia-Hai Lee
(74) *Attorney, Agent, or Firm* — Fox Rothschild LLP

(57) ABSTRACT

The present invention relates to a method of improving the resistance of a peptide or peptidomimetic to degradation by trypsin which comprises incorporating into said peptide or peptidomimetic a C-terminal capping group of formula (I): X—Y—Z (I) wherein X is a N atom, which may be substituted by a branched or unbranched $C_1$-$C_{10}$ alkyl or aryl group which group may incorporate up to 2 heteroatoms selected from N, O and S; Y represents a group selected from —$R_a$—$R_b$—, —$R_a$—$R_b$—$R_b$,- and —$R_b$—$R_b$—$R_a$— wherein $R_a$ is C, O, S or N, and $R_b$ is C; each of $R_a$ and $R_b$, may be substituted by $C_1$-$C_4$ alkyl groups or unsubstituted; and Z is a group comprising 1 to 3 cyclic groups each of 5 or 6 non-hydrogen atoms, 2 or more of the cyclic groups may be fused and one or more of the cyclic groups may be substituted; the Z. moiety incorporates a maximum of 15 non-hydrogen atoms; and wherein the bond between Y and Z is a covalent bond between $R_a$ or $R_b$ of Y and a non-hydrogen atom of one of the cyclic groups of Z.

13 Claims, 3 Drawing Sheets

Cleavage mode I

Cleavage mode II

METHODS OF PEPTIDE MODIFICATION

CROSS REFERENCE TO RELATED APPLICATIONS

This application is a 371 National Phase Application of PCT/GB08/04244 filed Dec. 22, 2008, which claims priority to GB Application No. 0724953.5 filed Dec. 20, 2007. Both applications are incorporated herein by reference.

The present invention relates to methods of modifying peptides to increase their resistance to enzymatic degradation, in particular to methods involving C-terminal modification of peptides to improve resistance to enzymatic degradation.

Peptides and proteins play a pivotal role both as the main effector molecules in the cells (enzymes) and in the control and in the regulation of the metabolic pathways. Furthermore, as peptides are polymers readily available from monomers with a substantial variety of chemical properties, peptides represents a vast and attractive pool of chemical diversity available to the medicinal chemist. Initially, the pharmaceutical companies were excited about the market potential of peptides for therapeutic use. However, several decades after the first chemical synthesis of a peptide hormone, very few peptides have been approved as drugs, often due, at least in part, to the stability of the peptide when administered.

Stability towards proteolytic degradation is very important for a drug. If the site of action is a metabolic active lesion (e.g. a wound), stability towards degradation in the lesion is of utmost importance. Furthermore, if a drug is to be orally active, stability towards degradation in the gastrointestinal (GI) tract is needed. Peptides are usually metabolised in the body by enzymatic hydrolysis of the amide bonds connecting the amino acids together. The enzymes responsible for this degradation falls into two general classes, the exopeptidases, which cleave the terminal amino acids, and the endopeptidases, which cleave at more or less specific sites within the peptide sequence.

The medicinal chemist has several tools to circumvent enzymatic degradation catalysed by proteolytic enzymes. The action of exopeptidases can usually be hindered by so called end-cappings, i.e. chemical modifications of the N- and C-terminal amino acids. Typical end-cappings include amidation of the C-terminus and acetylation or deamination of the N-terminus. Concerning the action of endopeptidases on peptides the usual method of inhibiting degradation is methylation of the amide nitrogen atom or inverting the stereochemistry of the amino acid(s) close to the cleavage site. The advantage with these methods is that the peptide retains most of its structure unaltered, which may lead to an unaffected bioactivity, although there are ample examples of changed and often diminished bioactivity caused by these changes.

A more radical approach to solve the problem of enzymatic degradation is to avoid hydrolysable bonds altogether by introducing peptidomimetic elements in the structure. The downside of the peptidomimetic approach is generally a much more complex synthesis, and that the much larger alteration of the original peptide structure often involved also give rise to a larger uncertainty in the prediction of the bioactivity. It should thus be evident that there is no panacea for obtaining stability against degrading enzymes, but that the medicinal chemist has a tool chest of various methods available each with its own merits and drawbacks.

The most important endopeptidases in the human GI tract are pepsin, found in the stomach, and trypsin and chymotrypsin, found in the upper part of the intestine. Both trypsin and chymotrypsin are classified mechanistically as serine proteases, but they differ both in three-dimensional structure and in substrate specificity. Chymotrypsin cleaves the peptide bond on the C-terminal side adjacent to large lipophilic amino acids (typically Phe), whereas trypsin cleaves on the C-terminal side of the cationic residues lysine and arginine.

Several therapeutically useful peptides contain cationic amino acids. Desmopressin, 1-Deamino-8-D-arginine-vasopressin (Mpa-Tyr-Phe-Gln-Asn-Cys-Pro-d-Arg-Gly-NH2), can serve as an example. Desmopressin is an orally active analogue of vasopressin (antidiuretic hormone) used in the treatment of diuresis associated with diabetes insipidus, nocturnal enuresis, and urinary incontinence. As resistance to enzymatic degradation in the GI tract is a prerequisite for oral bioavailability, trypsin represents the major hurdle in the GI tract for peptides containing cationic amino acids. A major contributor to the successful oral bioavailability of desmopressin is the conversion of the cationic arginine residue at position 8 into its D-enantiomer, which is not recognised and hence not degraded, by trypsin. The solution for circumventing trypsin activity used in desmopressin is certainly not general, the bioactivity of stereoisomeric peptides are usually vastly different (and very often inferior) to that of the natural stereoisomer.

Another important class of potentially clinically useful cationic peptides are the antimicrobial peptides (AMP's). AMP's are a structurally diverse class of cationic peptides with great potential in treating infections caused by resistant microorganisms. As AMP's are invariantly cationic they are also potential targets for trypsin. As trypsin is an endopeptidase requiring approximately a minimum of 6 amino acids in a peptide substrate, it has been assumed that very short AMPs should be stable towards endopeptidase enzymes. To the inventors' great surprise it turned out that a substantial number of short AMPs were degraded by trypsin.

In working to improve stability of peptides, in inventors have surprisingly found that a certain specific class of C-terminal capping groups significantly enhance resistance of peptides to cleavage by trypsin and therefore improve in vivo stability when peptides are administered orally.

Thus, according to one aspect, the present invention provides a method of improving the resistance of a peptide to degradation by trypsin which comprises incorporating into said peptide a C-terminal capping group of formula (I):

X—Y—Z    (I)

wherein

X is a N atom, which may be, but preferably is not, substituted by a branched or unbranched $C_1$-$C_{10}$ alkyl or aryl group, e.g. methyl, ethyl or phenyl, and this group may incorporate up to 2 heteroatoms selected from N, O and S;

Y represents a group selected from —$R_a$—$R_b$—$R_b$— and —$R_b$—$R_b$—$R_a$— wherein $R_a$ is C, O, S or N, preferably C, and $R_b$ is C;

each of $R_a$ and $R_b$ may be substituted by $C_1$-$C_4$ alkyl groups or unsubstituted, preferably Y is —$R_a$—$R_b$— (in which $R_a$ is preferably C) and preferably this group is not substituted, when Y is —$R_a$—$R_b$—$R_b$— or $R_b$—$R_b$—$R_a$— then one or more of $R_a$ and $R_b$ is substituted; and Z is a group comprising 1 to 3 cyclic groups each of 5 or 6 non-hydrogen atoms (preferably C atoms), 2 or more of the cyclic groups may be fused; one or more of the rings may be substituted and these substitutions may, but will typically not, include polar groups, suitable substituting groups include halogens, preferably fluorine or bromine and $C_1$-$C_4$ alkyl groups; the Z moiety incorporates a maximum of 15 non-hydrogen atoms, preferably 5-12, most preferably it is or comprises phenyl;

the bond between Y and Z is a covalent bond between $R_a$ or $R_b$ of Y and a non-hydrogen atom of one of the cyclic groups of Z.

Preferably the C-terminal capping group is or comprises 2-phenylethylamine, wherein the ethyl moiety and the nitrogen of the amine may be substituted as discussed above but preferably are not. The phenyl group may be substituted as described above, in particular by $C_1$-$C_4$ alkyl groups, but preferably it is not substituted.

Particularly preferred is a C-terminal capping group of formula (I):

X—Y—Z          (I)

wherein
X is an NH group;
Y is —$R_a$—$R_b$, wherein
$R_a$ is C, O, S or N, preferably C, and
$R_b$ is C;
each of $R_a$ and $R_b$ may be substituted by $C_1$-$C_4$ alkyl groups or unsubstituted;
and Z is as defined above.

Without wishing to be bound by theory, the three-dimensional shape and size of the C-terminal capping group, as well as the lipophilic character of the Z group of the C-terminal capping group are all believed to contribute to the provision of reduced susceptibility to degradation by trypsin.

In one embodiment, said method further comprises the step of measuring the susceptibility of said modified, i.e. capped, peptide to degradation by trypsin. The method may also include a step of measuring the susceptibility to degradation by trypsin of the same peptide but which lacks a C-terminal capping group according to the invention and optionally comparing those results.

It will be understood that where reference is made to 'incorporation into said peptide', the peptide may be synthesised so as to incorporate the C-terminal capping group from the outset. Alternatively it is possible, but not necessary, that a peptide will first be synthesised and then modified to incorporate the C-terminal capping group. The C-terminal capping group is incorporated into the peptide in such a way that X is covalently bound to the C-terminal amino acid. Preferably, a covalent bond is formed between the carbonyl-carbon of the C-terminal amino acid and the nitrogen of X. The C-terminal capping group is incorporated for the purpose of 'improving' the resistance of the peptide to degradation by trypsin (as compared to the same peptide without the C-terminal capping group). 'Degradation' refers to a single or multiple cleavage reactions by trypsin.

Alternatively viewed, the invention provides the use of a compound comprising or consisting of a chemical moiety of formula (I) as defined above, in the preparation of a peptide having increased resistance to trypsin degradation as compared to the same peptide which does not incorporate the moiety of formula (I) as a C-terminal capping group.

In a further aspect the invention provides a method of peptide production which comprises:
(a) measuring the susceptibility of a peptide of interest to degradation by trypsin;
(b) modifying said peptide by incorporation into said peptide a C-terminal capping group of formula (I) as defined above; and optionally
(c) measuring the susceptibility of said modified peptide to degradation by trypsin.

Optionally, prior to step (a) said method involves de novo synthesis of a peptide.

Further aspects of the present invention include peptides prepared according to the methods of the invention for use in therapy, in particular for oral treatment of disease or infection for example as anti-microbial agents and methods of oral treatment of disease or infection.

The peptides which are modified according to the present invention have a cationic amino acid having the standard L configuration as their C-terminal residue, referred to herein as position (C), preferably lysine or arginine but histidine or non-genetically coded amino acids carrying a positive charge at pH 7.0 are also covered. Suitable non-genetically coded amino acids and modified amino acids which also provide a cationic amino acid include analogues of lysine, arginine and histidine such as homolysine, ornithine, diaminobutyric acid, diaminopimelic acid, diaminopropionic acid and homoarginine as well as trimethyllysine and trimethylornithine.

At position (C-1) the peptides typically have an amino acid with a large lipophilic R group, preferably the R group has at least 9, more preferably at least 10 or 11 non-hydrogen atoms, e.g., 9-20, preferably 9-17 non-hydrogen atoms, typically the R group contains 2 or more cyclic groups which may be fused or connected, these cyclic groups will typically comprise 5 or 6 non-hydrogen atoms, preferably 5 or 6 carbon atoms A further cationic residue may typically be present at position (C-2).

The peptides can be of any length from 3 amino acids and upwards, typically from 3-25, e.g. 3-18, preferably 3-12, more preferably 3-9 amino acids in length.

A preferred class of peptides are antimicrobial peptides with a lytic effect on microbial cell membranes. Such molecules are disclosed, for example, in WO 01/66147. These peptides and other, larger, antimicrobial peptides are often termed 'cationic', typically possessing 3 or more groups which carry a positive charge at pH7.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the invention.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OPClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

In addition to peptides, the C-terminal capping group described herein may be used to improve the stability of peptidomimetic compounds, thus, in a further aspect the present invention provides a method of improving the resistance of a peptidomimetic compound to degradation by trypsin which comprises incorporation into said peptidomimetic a C-terminal capping group of formula (I) as defined above.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. Suitable amide bond surrogates include the following groups: N-alkylation (Schmidt, R. et al., Int. J. Peptide Protein Res., 1995, 46,47), retro-inverse amide (Chorev, M. and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

The C-terminal capping groups of the present invention include a lipophilic moiety and this is advantageous when it is desired to retain or improve the lipophilic character of the peptide which is modified. For example, antimicrobial peptides typically advantageously incorporate lipophilic groups.

In all cases, it is possibly to assess the stability of a molecule by an in vitro assay of its resistance to degradation by trypsin. A suitable method includes reverse phase HPLC and this is described herein in the Examples. Using this assay it is possible to compare the resistance of two molecules, e.g., a peptide with and without the C-terminal capping group described herein to confirm improvement in resistance to degradation and thereby stability. Preferably the stability is increased at least 2 fold, preferably at least 3, 4 or 5 fold, most preferably at least 6 fold.

Stability may be expressed in terms of biological half life, i.e. the amount of time it takes for half of the total amount of peptide to be broken down. When half life is assayed in vitro, it is dependent on the initial concentration of the peptide present in the assay. It is therefore important to compare the half lives of peptides under identical or at least comparable assay conditions. Biological half life is thus not an absolute quality of a particular molecule, but a relative quality.

The invention will now be further described with reference to the following non-limiting Figures and Example in which FIG. 1 shows a general scheme for the preparation of amino acid derivatives which may be incorporated into the peptides described herein.

EXAMPLES

Example 1

Peptide Preparation and Measurement of Degradation by Trypsin

Chemicals

Figure 1:
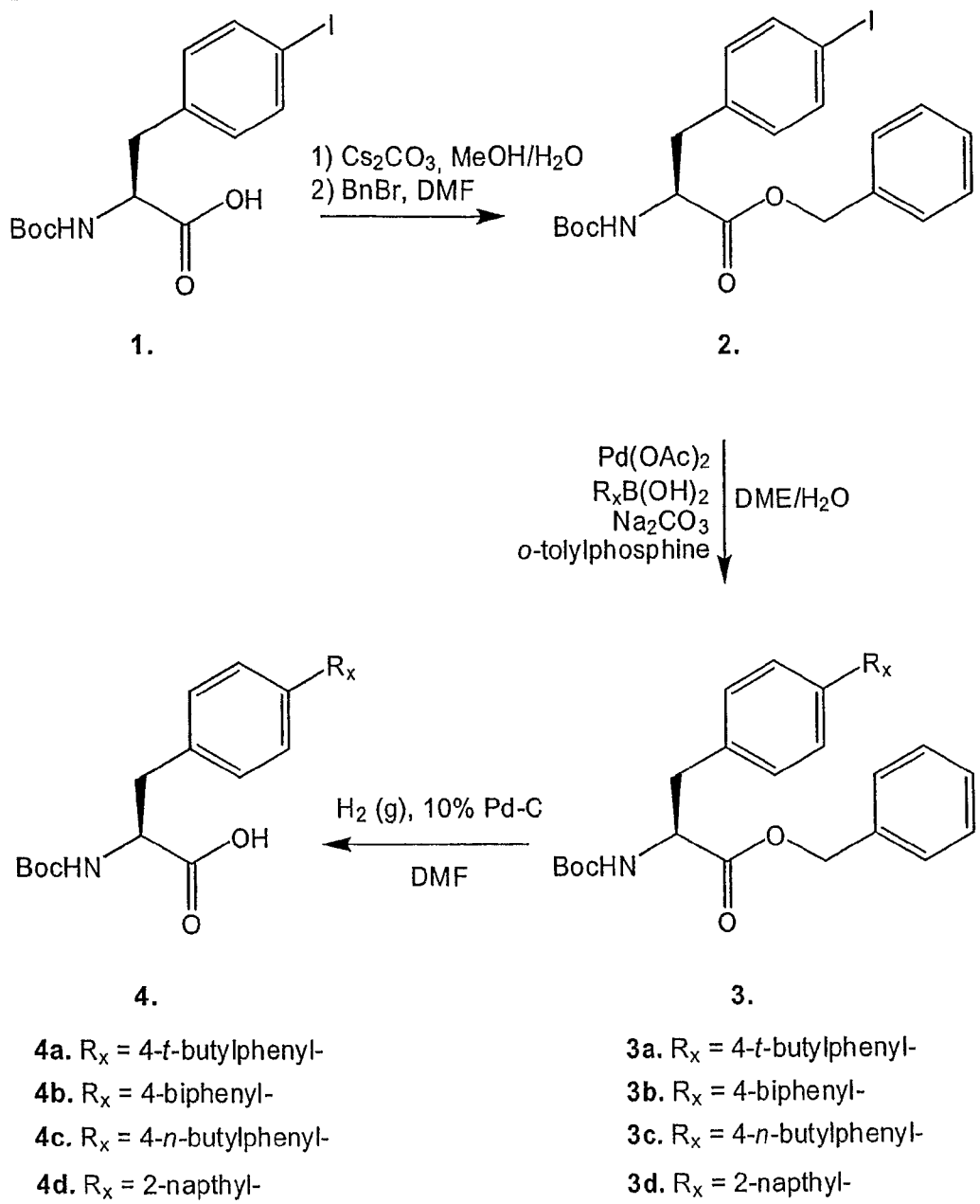

Essentially salt-free trypsin from bovine pancreas, (T8802, 10000-15000 BAEE units/mg protein) was supplied by Sigma-Aldrich. Protected amino acids were purchased from Bachem AG or Aldrich. Chemicals were purchased from Fluka Acros. Merck, Riedel-de Haen or Aldrich Preparation of Amino Acids Non-commercially available amino acid derivatives were prepared according to the general scheme outlined in FIG. 1 (Scheme 1.)

Benzylation of Boc-4-iodophenylalanine (2).

Boc-4-iodophenylalanine (1, 1 eq.) was dissolved in 90% methanol in water and neutralized by addition of cesium carbonate until it was a weakly alkaline (determined with litmus paper). The solvent was removed by rotary evaporation, and any remaining water in the cesium salt of Boc-4- iodophenylalanine was further reduced by repeated azeotropic distillation with toluene. The resulting dry salt was dissolved in dimethylformamide (DMF). Benzyl bromide (1.2 eq.) was added and the resulting mixture was stirred for 6-8 h. The solvent was removed under reduced pressure, producing an oil, containing the title compound (2). The oil was separated between ethyl acetate and acetic acid (15% v/v) and the organic phase was washed with equal volumes of citric acid solution (5% v/v, two times), a saturated solution of $NaHCO_3$ and brine. The title compound was isolated as a pale yellow oil in 85% yield after purification by flash chromatography using $CH_2Cl_2$:ethyl acetate (95:5 v/v) as eluent. Crystalline benzyl Boc-4-iodophenylalanine could be obtained by recrystallisation from n-heptane.

General Procedure for Suzuki-Miyaura Couplings

Benzyl Boc-4-iodophenylalanine (1 eq.), arylboronic acid (1.5 eq.), sodium carbonate (2 eq.), palladium acetate (0.05 eq.) and tri ortho-tolylphosphine (0.1 eq.) was added to a degassed mixture of dimethoxyethane (6 ml/mmol amino acid) and water (1 ml/mmol amino acid). The reaction mixture was kept under argon and heated to 80° C. for 4-6 h. After cooling to room temperature, the mixture was filtered through a short pad of silica gel and sodium carbonate. The filter cake was further washed with ethyl acetate and combined with the other fraction before the solvents were removed under reduced pressure. The products were purified using flash chromatography using mixtures of ethyl acetate and n-hexane as eluent.

Preparation of Boc-Bip(t-Bu)-OBn (3a).

The title compound was prepared in 79% yield from 4-t-butylphenylboronic acid using the general procedure for Suzuki couplings. 3a was isolated after flash chromatography employing ethyl acetate:n-hexane eluent (80:20 v/v) as eluent.

Preparation of Boc-Bip(4-Ph)-OBn (3b).

The title compound was prepared in 61% yield from 4-biphenylboronic acid using the general procedure for Suzuki couplings. 3b was isolated by recrystallisation of the crude product from n-heptane.

Preparation of Boc-Bip(n-Bu)-OBn (3c).

The title compound was prepared in 53% yield from 4-n-butylphenylboronic acid using the general procedure for Suzuki couplings. 3c was purified using 80:20 ethyl acetate:n-hexane as eluent.

Preparation of Boc-Phe(4-(2-Naphtyl))-OBn (3d).

The title compound was prepared in 68% yield from 2-naphtylboronic acid using the general procedure for Suzuki couplings. 3d was isolated by recrystallisation of the crude product from n-heptane.

General Procedure for Deesterification of Benzyl Esters.

The benzyl ester was dissolved in DMF and hydrogenated for 2 days at ambient pressure and temperature using 10% Pd on carbon as catalyst. At the end of the reaction, the catalyst was removed by filtration and the solvent removed under reduced pressure. The free acid was isolated by recrystallisation from diethyl ether.

Preparation of Boc-Bip(4-t-Bu)-OH (4a).

The title compound was prepared in 65% yield from 3a using the general procedure for deesterification.

Preparation of Boc-Bip(4-Ph)-OH (4b).

The title compound was prepared in 61% yield from 3b using the general procedure for deesterification.

Preparation of Boc-Bip(4-n-Bu)-OH (4c).

The title compound was prepared in 61% yield from 3c using the general procedure for deesterification.

Preparation of Boc-Phe(4-(2-Naphtyl))-OH (4d).

The title compound was prepared in 68% yield from 3d using the general procedure for deesterification.

General Procedure for Solution Phase Peptide Synthesis Using HBTU as Coupling Reagent The peptides were prepared in solution by stepwise amino acid coupling using Boc protecting strategy according to the following general procedure. The C-terminal peptide part with a free amino group (1 eq.), Boc protected amino acid (1.05 eq.) and 1-HOBt (1.8 eq.) were dissolved in DMF (2-4 ml/mmol of amino component) before addition of DIPEA (4.8 eq.). The mixture was cooled on ice before HBTU (1.2 eq.) was added and the reaction mixture was agitated at ambient temperature for 1-2 h. The reaction mixture was diluted with ethyl acetate and washed with a citric acid solution (5% v/v), a saturated $NaHCO_3$ solution and brine. The solvent was removed under vacuum and the Boc protecting group of the resulting peptide was deprotected in the dark using 95% TFA or acetyl chloride in anhydrous methanol.

Solution phase amide formation using PyClop Synthesis of $NH_2$-Arg-N$(CH_2Ph)_2$.

For further information see Coste, J., Frerot, E., and Jouin, P. (1994) Coupling N-Methylated Amino-Acids Using Pybrop and Pyclop Halogenophosphonium Salts—Mechanism and Fields of Application. J. Org. Chem. 59, 2437-2446). A solution of Boc-Arg-OH (1 eq.), $NH(CH_2Ph)_2$ (1.1 eq.) and PyCloP (1 eq.) in dry $CH_2Cl_2$ (2 ml) and DMF (1 ml). The solution was cooled on ice and DIPEA (2 eq.) was added under stirring. The solution was stirred for 1 h at room temperature. The reaction mixture was evaporated, redissolved in ethyl acetate and washed with citric acid solution (5% v/v), a saturated solution of $NaHCO_3$ and brine. The solvent was removed under reduced pressure and the Boc protecting group of the resulting amino acid derivative was removed in the dark using 95% TFA.

Peptide Purification and Analysis—RP-HPLC

The peptides were purified using reversed phase HPLC on a Delta-Pak (Waters) $C_{18}$ column (100 Å, 15 μm, 25×100 mm) with a mixture of water and acetonitrile (both containing 0.1% TFA) as eluent. The purity of the peptides was further analysed by RP-HPLC using an analytical Delta-Pak (Waters) $C_{18}$ column (100 Å, 5 μm, 3.9×150 mm) and positive ion electrospray mass spectrometry on a VG Quattro quadrupole mass spectrometer (VG Instruments Inc., Altringham, UK).

Measurements and Calculation of Peptide Half-Life

Each peptide was dissolved in a 0.1 M $NH_4HCO_3$ buffer (pH 6.5) to yield a final peptide concentration of 1 mg/ml. A trypsin solution was prepared by dissolving 1 mg of trypsin in 50 ml 0.1 M $NH_4HCO_3$ buffer (pH 8.2). For the stability determination, 250 μl freshly made trypsin solution and 250 μl peptide solution were incubated in 2 ml of 0.1 M $NH_4HCO_3$ buffer (pH 8.6) at 37° C. on a rocking table. Aliquots of 0.5 ml were sampled at different time intervals, diluted with 0.5 ml water:acetonitrile (60:40 v/v) containing 1% TFA and analysed by RP-HPLC as described above. Samples without trypsin addition taken at 0 h and after 20 h at 37° C. were used as negative controls. Integration of the peak area at 254 nm for samples taken during the first 5 hours of the assay was used to generate the $t_{1/2}$ using Medical Calculator from Cornell University. The plotted kinetic profiles were made on GraphPad Prism 4c.

The identity of the metabolites from the tryptic degradation was either determined by preparative trypsin degradation of the peptide, purification and structural determination by ESMS, or by chemical synthesis of authentic reference samples.

Figure 2:
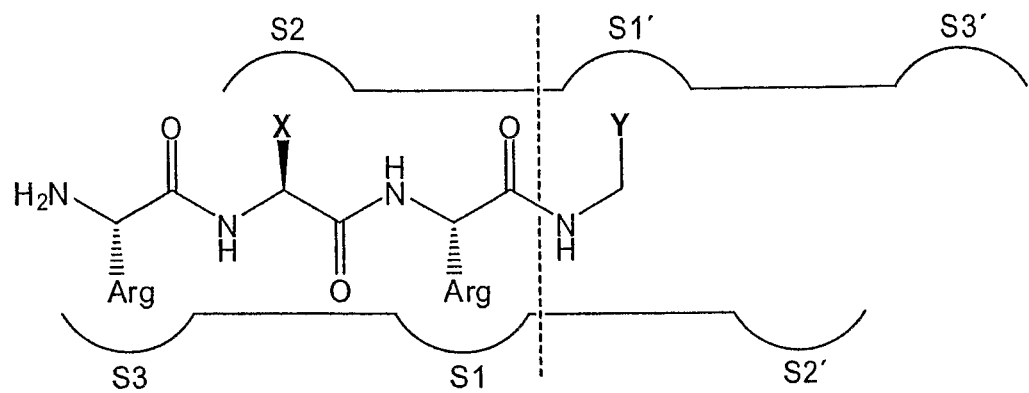
FIG. 2 shows the two possible modes by which trypsin could cleave small peptides.
Figure 2:
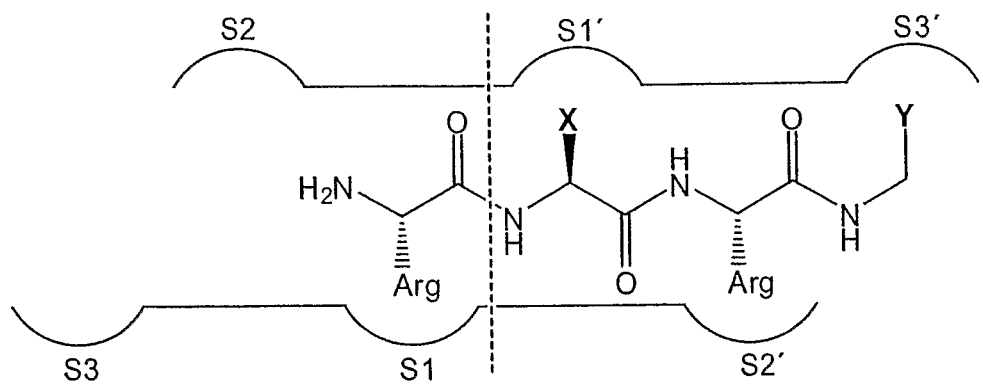

Trypsin cleaves peptides at the C-terminal side of positively charged residues; arginine, lysine and histidine. All peptides tested contain two arginine residues, one at the C-terminus and one at the N-terminus. The peptides thus contain two different conceivable scissile bonds; either between the C-terminal arginine and the X—Y—Z-group corresponding to cleavage mode I in FIG. 2, or alternatively between the N-terminal arginine and the C-1-residue corresponding to cleavage mode II. The inventors consequently decided to monitor the rate of peptide cleavage by the use of HPLC, as this method not only is capable of measuring the rate, but simultaneously is capable of determining the mode of cleavage by characterizing the structure of the cleavage products.

A library of peptides was designed to explore the influence of the C-terminal capping moiety on the stability towards trypsin. The results are shown in Table 1. Table 1 shows that C-terminal capping groups according to the present invention increased the stability of various peptides, by at least a factor of two, but often by a factor of seven or even by an order of magnitude.

Figure 3:
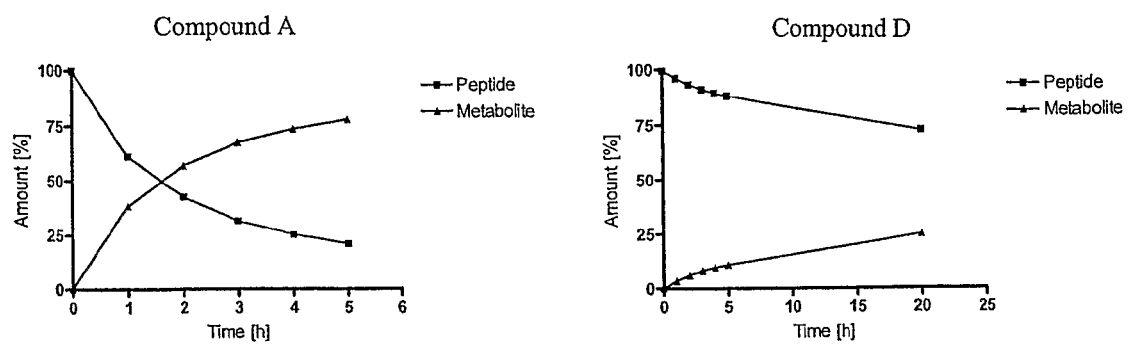
FIG. 3 shows variation of peptide and metabolite concentration versus time as a result of treatment with trypsin. Medical Calculator from Cornell University was used to calculate the half-life based on data gathered during the first five hours of degradation.

FIG. 3 shows plots of the relative amounts of peptide and metabolite (H-Arg-lipophilic amino acid-Arg-OH) versus time for compound A, which does not possess a C-terminal capping group according to the present invention, and compound D, which does possess such a C-terminal capping group.

TABLE 1

| Compound | Peptide sequence R—Xaa—R, Xaa being | C-terminal capping group | Half life t1/2 (h) |
|---|---|---|---|
| A | | | 2 |
| B | | | 35 |
| C | | | 9 |
| D | | | 30 |
| E | | | 1 |
| F | | | 7 |
| G | | | 7 |

TABLE 1-continued

| Compound | Peptide sequence R—Xaa—R, Xaa being | C-terminal capping group | Half life t1/2 (h) |
|---|---|---|---|
| H | 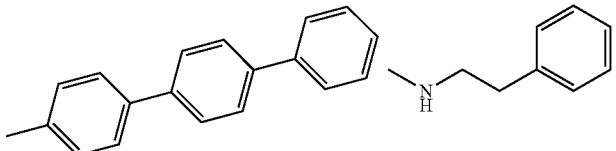 | | >24 |
| I | | | 3 |
| J | | | 30 |

Example 2

Preparation of a Further Peptide Incorporating a Capping Group as Described Herein A further compound was prepared according to the methods of the invention and Minimal Inhibitory Concentration (MIC) values obtained against a range of bacteria.

H-Arg-Tbt-Arg-NH(CH$_2$)$_2$ (2-Br-phenyl)

Saponification of Boc-Arg-Tbt-Arg-OMe

LiOH.H$_2$O (373 mg, 8.9 mmol) was added to a colorless solution of BocArgTbtArg-OMe.2HCl (2.5 g, 2.9 mmol, prepared as described in WO 01/66147) in a H$_2$O (5 ml) THF (20 ml) mixture and the reaction was stirred at room temperature for 30 min during which it rapidly developed a yellow color. Dilute HCl (52 ml) and saturated brine (35 ml) were added and the resulting mixture extracted with DCM. The DCM was evaporated and the organic material redissolved in DCM, dried over Na$_2$SO$_4$, filtered and concentrated. Obtained mass of BocArgTbtArg-OH: 2.46 g, 93%.

PyBOP Mediated Coupling

The TFA salt of BocArgTbtArgCO$_2$H (365 mg, 0.35 mmol) was mixed with 2-bromo phenyl ethyl amine (53 µl) in DMF (0.9 ml) and DIPEA (120 µl) was added. The reaction mixture was stirred at room temperature for 5 min before PyBOP (194 mg, 0.37 mmol) was added and then left for 3 hours. Prior to the workup the mixture was diluted with EtOAc (20 ml) and washed with 2×30 ml 5% citric acid sol., 2×30 ml 5% NaHCO$_3$ sol., 30 ml sat. brine, followed by drying over Na$_2$SO$_4$, filtration and concentration. The crude product was isolated as an oil (432 mg) containing a byproduct from the coupling reagent. The Boc group was removed by dissolving the crude in 15 ml 4 M HCl in 1,4-dioxane and stirring it for 30 min at room temperature before concentration and final purification by reversed phase chromatography.

Purity: >95%, Electrospray mass spectrometry (m/z, protonated molecular iom): 866.48/868.56 (calculated), 866.5/868.5 (observed).

Microbiological Data

Minimal inhibitory concentration (mg/l),

| | H-Arg-Tbt-Arg-NH—Y—Z | | | |
|---|---|---|---|---|
| Y—Z | E. coli | S. aureus | MRSA | Str. pyogenes |
| —(CH$_2$)$_2$-(2-BrPh) | 6 | 3 | 3 | 3 |

The invention claimed is:

1. A method of improving the resistance of a peptide which has a cationic amino acid at its C-terminus or a peptidomimetic which has a cationic amino acid at its C-terminus to degradation by trypsin which comprises:
    (a) incorporating into said peptide or peptidomimetic a C-terminal capping group of formula (I):

X—Y—Z   (I)

wherein
    X is a N atom, which may be substituted by a branched or unbranched C$_1$-C$_{10}$ alkyl or aryl group which group may incorporate up to 2 heteroatoms selected from N, O and S;
    Y represents —R$_a$—R$_b$—, wherein
    R$_a$ is C, O, S or N, and
    R$_b$ is C; each of R$_a$ and R$_b$ may be substituted by C$_1$-C$_4$ alkyl groups or unsubstituted; and
    Z is a group comprising 1 to 3 unsubstituted cyclic groups each of 5 or 6 non-hydrogen atoms, and 2 or more of the cyclic groups may be fused; the Z moiety incorporates a maximum of 15 non-hydrogen atoms; and wherein the bond between Y and Z is a covalent bond between R$_a$ or R$_b$ of Y and a non-hydrogen atom of one of the cyclic groups of Z: and
    (b) measuring the susceptibility of said capped peptide or peptidomimetic to degradation by trypsin.

2. A method of peptide production which comprises:
    (a) measuring the susceptibility of a peptide of interest which has a cationic amino acid at its C-terminus to degradation by trypsin;

(b) modifying said peptide by incorporation into said peptide a C-terminal capping group of formula (I):

X—Y—Z  (I)

wherein

X is a N atom, which may be substituted by a branched or unbranched $C_1$-$C_{10}$ alkyl or aryl group which group may incorporate up to 2 heteroatoms selected from N, O and S;

Y represents —$R_a$—$R_b$—, wherein $R_a$ is C, O, S or N, and $R_b$ is C; each of $R_a$ and $R_b$ may be substituted by $C_1$-$C_4$ alkyl groups or unsubstituted; and Z is a group comprising 1 to 3 unsubstituted cyclic groups each of 5 or 6 non-hydrogen atoms, and 2 or more of the cyclic groups may be fused; the Z moiety incorporates a maximum of 15 non-hydrogen atoms; and wherein the bond between Y and Z is a covalent bond between $R_a$ or $R_b$ of Y and a non-hydrogen atom of one of the cyclic groups of Z; and optionally (c) measuring the susceptibility of said modified peptide to degradation by trypsin.

3. The method as claimed in claim 1 or 2 wherein X is unsubstituted.

4. The method as claimed in claim 1 or 2 wherein $R_a$ is C.

5. The method as claimed in claim 1 or 2 wherein Y is —$R_a$—$R_b$—and unsubstituted.

6. The method as claimed in claim 5 wherein Y is —$CH_2$—$CH_2$—.

7. The method as claimed in claim 1 or 2 wherein Z is phenyl.

8. The method as claimed in claim 1 or 2 in which -X-Y-Z together are —$NHCH_2CH_2Ph$.

9. The method as claimed in claim 1 or 2 wherein the peptide has lysine or arginine at its C-terminus.

10. The method as claimed in claim 9 wherein the peptide has an amino acid with a lipophilic R group adjacent to the C-terminal amino acid.

11. The method as claimed in claim 10 wherein the lipophilic R group has 9-20 non-hydrogen atoms.

12. The method as claimed in claim 10 wherein the lipophilic R group has 2 or more cyclic groups.

13. The method as claimed in claim 1 or 2 wherein the peptide is 3-18 amino acids in length.

* * * * *